US005877299A

United States Patent [19]
Thomas et al.

[11] Patent Number: 5,877,299
[45] Date of Patent: Mar. 2, 1999

[54] METHODS FOR PREPARING ENRICHED HUMAN HEMATOPOIETIC CELL PREPARATIONS

[75] Inventors: Terry Thomas; Peter Lansdorp, both of Vancouver, Canada

[73] Assignee: Stemcell Technologies Inc., Vancouver, Canada

[21] Appl. No.: 491,175

[22] Filed: Jun. 16, 1995

[51] Int. Cl.[6] ................................................ C07K 1/00
[52] U.S. Cl. ............................ 530/413; 435/2; 435/372; 530/413; 530/388.73; 530/388.75; 530/388.7
[58] Field of Search .......................... 435/7.24, 2, 372, 435/366; 530/388.7, 388.73, 388.75, 391.1, 413

[56] References Cited

U.S. PATENT DOCUMENTS

| | | | |
|---|---|---|---|
| 4,752,582 | 6/1988 | Vanderlaan et al. | 435/240.27 |
| 4,868,109 | 9/1989 | Lansdorp | 435/28 |
| 5,087,570 | 2/1992 | Weissman et al. | 435/240.1 |
| 5,137,809 | 8/1992 | Loken et al. | 435/7.21 |

OTHER PUBLICATIONS

Knapp, W. et al. eds, Oxford University Press. Oxford, p.818, Civin, C. et al., Report on the CD34 cluster workshop, In: Leucocyte typing IV, White Cell Differentiation Antigens, (1989).
Ishizawa, L. et al., In: Hematopoietic Stem Cells: The Mulhouse Manual eds. Winder, E. et al., 171–182 1993.
Shpall, E.J., et al., J. of Clinical Oncology, 12:28–36, 1994.
Winslow, J.M., et al., Bone Marrow Transplantation, 14:265–271, 1994.
Thomas, T.E., Cancer Research, Therapy and Control, 4(2): 119–128), 1994.
Linch, D.C. and Nathan, D.G., Nature 312 20/27: 775–777, 1984.
Sieff, C.A., et al., Science 230: 1171–1173, 1985.
Kannourakis, G. and Bol, S., Exp. Hematol, 15:1103–1108, 1987.
Carlo–Stella et al., Blood 84, 10 supple.:104a, 1994.
Reading, C., et al., Blood 84, 10supple.:399a, 1994.
Hodgson, G.S. & Bradley, T.R., Nature, vol. 281, pp. 381–382; Oct. 1987.
Visser et al., J. Exp. Med., vol. 59, pp. 1576–1590, 1984.
Spangrude et al., Science, vol. 241:58–62, 1988.
Szilvassy et al., Blood, 74:930–939, 1989.
Ploemacher, R.E. & Brons, R.H.C., Exp. Hematol., 17:263–266, 1989.
Udomsakdi et al., Exp. Hematol., 19:338, 1991.
Sutherland et al., Proc. Natl. Acad. Sci., 87:3584, 1990.
Craig, et al., British Journal of Haematology, 88:24–30, 1994.

(List continued on next page.)

*Primary Examiner*—Sheela Huff
*Assistant Examiner*—Julie E. Reeves
*Attorney, Agent, or Firm*—Merchant, Gould, Smith, Edell, Welter & Schmidt

[57] ABSTRACT

The present invention relates to an antibody composition which contains antibodies specific for glycophorin A, CD3, CD24, CD16, CD14, and optionally CD45RA, CD36, CD56, CD2, CD19, CD66a and/or CD66b. A process is also provided for enriching and recovering human hematopoietic progenitor cells and stem cells in a sample containing human hematopoietic differentiated, progenitor, and stem cells. The process involves reacting the sample with an antibody composition containing antibodies capable of binding to the antigens glycophorin A, CD3, CD24, CD16, and CD14, and optionally CD45RA, CD36, CD56, CD2, CD19, CD66a and/or CD66b under conditions so that cell conjugates are formed between the antibodies and differentiated cells having the antigens glycophorin A, CD3, CD24, CD16, and CD14, and optionally CD45RA, CD36, CD56, CD2, CD19, CD66a and/or CD66b on their surfaces. The cell conjugates are removed and a cell preparation is obtained which is enriched in human hematopoietic progenitor cells and stem cells. The invention also relates to kits for carrying out this process and to the cell preparations prepared by the process.

15 Claims, 2 Drawing Sheets

OTHER PUBLICATIONS

Lansdorp, P.AI. and Dragowska, W., J. Exp. Med. 175:1501–1509, 1992.

Sutherland, H.J., et al., Blood 74:1563–1570, 1989.

Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation–Clinical Progress, New Technologies and Gene Therapy, San Diego, CA.

Berenson et al., Journal of Immunological Methods 91:11–19, 1986.

Nordon et al., Cytometry 16:25–33, 1994.

Molday, R.S. and MacKenzie, D., J. Immunol. Methods 52:353, 1982.

Thomas et al., J. Hematother. 2:297, 1993.

Thomas, T.E. et al., J. Immunol Methods 154:245;252, 1992.

Lansdorp, P.M. and Thomas, T.E., Mol. Immunol. 27:659–666, 1990.

Gabbianelli et al Science vol 249 1561–1564, Sep. 1990.

Saeland et al Exp Haematol vol 20 24–33, 1992.

Verfaillie et al j Exp Med vol 172 509–520, Aug. 1990.

Berenson et al Blood vol 67 No 2 509–515, Feb. 1986.

Greenwalt et al Blood vol 80 No 5 1105–1115, Sep. 1992.

Penninger et al Immunol Review No 135 183–214, 1993.

Fischer et al J Immunology vol 144 No 2 638–641, Jan. 1990.

Kuijpers et al J Immunology vol 151 No 9 4934–4940, Nov. 1993.

Kuijpers et al J Cell Biol vol 118 No 2 457–466, Jul. 1992.

Thoma et al Blood vol 83(8) 2103–2124, Apr. 1994.

van der Schoot et al Blood VOI 76(9) 1853–1859, Nov. 1990.

Smeland et al Leukemia vol 6 (8) 845–852 Aug. 1992.

A

B

METHODS FOR PREPARING ENRICHED HUMAN HEMATOPOIETIC CELL PREPARATIONS

FIELD OF THE INVENTION

The present invention relates to novel antibody compositions, and processes and kits for preparing cell preparations containing human hematopoietic cells, and the use of the cell preparations. The invention also relates to purified human hematopoietic cell preparations.

BACKGROUND OF THE INVENTION

Blood cells have a relatively short life span and need to be replenished throughout life. In adults, blood cell formation or hematopoiesis takes place in the bone marrow, but blood-forming stem cells can also be found in peripheral blood. Hematopoietic cells represent a hierarchy of proliferating and differentiating cells. The most abundant are the differentiating or lineage committed cells. These cells have limited or no proliferative capacity and represent specialized end cells that are found in blood, and their immediate precursors.

The immediate precursors of the differentiating cells are the progenitor cells. Most of these cells are restricted to differentiate along a single lineage but they may have quite extensive proliferative capacity. Progenitor cells appear morphologically as blast cells, and they typically do not have specific features of the hematopoietic lineage to which they are committed.

Progenitor cells are derived from stem cells. Stem cells have been historically defined by their ability to self-renew as well as to generate daughter cells of any of the hematopoietic lineages. The presence of stem and progenitor cells may be detected by their ability to produce colony-forming cells in culture, They may also be detected by screening for the CD34 antigen which is a positive marker for early hematopoietic cells including colony forming cells and stern cells. At present, the long term culture initiating cell (LTCIC) assay appears to be the best way to detect stem cells, or at least the most primitive progenitor cells, using tissue culture methodologies.

There is a continued interest in developing stem cell purification techniques. Pure populations of stem cells will facilitate studies of hematopoiesis. Transplantation of hematopoietic cells from peripheral blood and/or bone marrow is also increasingly used in combination with high-dose chemo- and/or radiotherapy for the treatment of a variety of disorders including malignant, nonmalignant and genetic disorders. Very few cells in such transplants are capable of long-term hematopoietic reconstitution, and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogenic grafts, and tumour cells in autologous transplants that may cause recurrence of the malignant growth.

Hematopoietic cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic approaches to separating cell populations from bone marrow and peripheral blood using monoclonal antibodies. They differ in whether it is the desired or undesired cells which are distinguished/labeled with the antibody(s). In positive selection techniques the desired cells are labeled with antibodies and removed from the remaining unlabeled/unwanted cells. In negative selection, the unwanted cells are labeled and removed. Antibody/complement treatment and the use of immunotoxins are negative selection techniques, but FACS sorting and most batch wise immunoadsorption techniques can be adapted to both positive and negative selection. In immunoadsorption techniques cells are selected with monoclonal antibodies and preferentially bound to a surface which can be removed from the remainder of the cells e,g. column of beads, flasks, magnetic particles. Immunoadsorption techniques have won favour clinically and in research because they maintain the high specificity of targeting cells with monoclonal antibodies, but unlike FACSorting, they can be scaled up to deal directly with the large numbers of cells in a clinical harvest and they avoid the dangers of using cytotoxic reagents such as immunotoxins, and complement.

Current positive selection techniques for the purification of hematopoietic stem cells target and isolate cells which express CD34 (approximately 1–2% of normal bone marrow) (Civin, C. I., Trischmann, T. M., Fackler, M. J., Bernstein, I. D., Buhring, H. J., Campos, L. et al. (1989) Report on the CD34 cluster workshop, In: Leucocyte typing IV, White Cell Differentiation Antigens. Knapp, W., Dorken, B., Gilks, W. R., Reiber, E. P., Schmidt, R. E., Stein, H., and Kr. von den Borne, AE.G Eds., Oxford University Press. Oxford, pp.818). Thus, the potential enrichment of hematopoietic stem cells using this marker alone is 50 fold. Available techniques typically recover 30–70% of the $CD34^+$cells in the start suspension and produce an enriched suspension which is 50–80% $CD34^+$(Ishizawa, L. et al., In: Hematopoietic Stem Cells: The Mulhouse Manual eds. Wunder, E., Sovalat, H. Henon, P., and Serke, S. AlphaMed Presa, Ohio pp171–182; Shpall, E. J., et al. (1994), J. of Clinical Oncology 12:28–36; Winslow, J. M., et al. (1994), Bone Marrow Transplantation 14:265–271; Thomas, T. E., (1994), Cancer Research, Therapy and Control 4(2):119–128). The positive selection procedures suffer from many disadvantages including the presence of materials such as antibodies and/or magnetic beads on the $CD34^+$ cells, and damage to the cells resulting from the removal of these materials.

Negative selection has been used to remove minor populations of cells from clinical grafts. These cells are either T-cells or tumour cells that pose a risk to the transplant recipient. The efficiency of these purges varies with the technique and depends on the type and number of antibodies used. Typically, the end product is very similar to the start suspension, missing only the tumor cells or T-cells.

Transplants of purified stern cells without differentiated or lineage committed cells will give short and long-term hematopoietic support (Shpall, E. J., et al. (1994), J. of Clinical Oncology 12:28–36). Since differentiated cells make up a vast majority of the cells in bone marrow and blood, depletion of these cells produces a much smaller cell suspension. The number of cells in the final product and the degree of enrichment of progenitor/stem cells will depend on the efficiency of the antibody targeting and the removal of labeled cells.

There are several studies that enrich for hematopoietic stem cells by depleting lineage committed cells but all require a number of positive or negative selection steps to achieve the desired degree of enrichment (50 fold). Early studies required prior density separation and extensive incubations to remove adherent cells (Linch, D. C., and Nathan, D. G. (1984), Nature 312 20/27:775–777; Sieff, C. A., et al. (1985), Science 230:1171–1173; Kannourakis, G. and Bol, S. (1987) Exp. Hematol 15:1103–1108.). More recent techniques have not been simplified; involving density separation steps followed by two partial lineage depletions (Winslow, J. M., et al. (1994), Bone Marrow Transplantation 14:265–271) or a partial lineage depletion using panning or FACS followed finally by positive selection using FACS (Carlo-Stella et al. 1994, Blood 84, 10 supple.:104a; Reading, C., et al. (1994), Blood 84, 10supple.:399a). Most of these methods for lineage depletion lack effective antibody combinations against myeloid cells, erythrocytes and/or B-cells.

U.S. Pat. No. 5,087,570 describes a process for preparing a hematopoietic cell composition using a combination of positive and negative selection, The process relies on the use of antibody to the Sca-1 antigen which is associated with murine clonogenic bone marrow precursors of thymocytes and progeny T-cells. The Sca-1 antibody is not useful in isolating human hematopoietic cells.

U.S. Pat. No. 5,137,809 describes a method and kit for identifying and analyzing lineages and maturational stages in normal hematopoietic cells. The method uses a first monoclonal antibody labeled with a fluorochrome to react with all leukocytes in a sample, and a second monoclonal antibody labeled with a second fluorochrome to react with a subpopulation of leukocytes.

SUMMARY OF THE INVENTION

The present inventors have developed an antibody composition for use in preparing cell preparations enriched for human hematopoietic stem cells and progenitor cells. The antibodies in the antibody composition are specific for selected markers associated with differentiated cells. In particular, the present inventors have found using a negative selection technique that an antibody composition containing antibodies specific for glycophorin A, CD3, CD24, CD16, CD14 and optionally CD45RA, CD36, CD2, CD19, CD56, CD66a, and CD66b, gives a cell preparation highly enriched for human hematopoietic and progenitor cells. Maximum enrichment of early progenitor and stem cells (CD34$^+$, CD38$^-$ cells) was observed when anti-CD45R and anti-CD36 were included in the antibody composition.

The present inventors have shown that the use of the antibody composition of the present invention in a negative selection technique, to prepare a cell preparation which is enriched for hematopoietic stem cells and progenitor cells offers many advantages over conventional techniques. The antibody composition applied in one step to a sample of peripheral blood, bone marrow, cord blood or frozen bone marrow, results in a greater than 50% recovery of human hematopoietic progenitor/stem cells with approximately a 3 log depletion of differentiated cells. This high level of enrichment obtained using the antibody composition of the invention, does not require additional enrichments steps, which would result in loss of, or damage to, progenitor and stem cells. The recovery of CD34$^+$ cells, CD34$^+$CD38$^-$ cells, colony forming cells, and LTCIC, is also much higher than with conventional multistep techniques.

The enrichment and recovery of human hematopoietic progenitor and stem cells using the antibody composition of the invention in a negative selection technique has many advantages over conventional positive selection techniques. As mentioned above, a highly enriched progenitor/stem cell preparation can be obtained using a single step. The human progenitor and stem cells obtained using the antibody composition of the invention are not labeled or coated with antibodies or modified making them highly suitable for transplantation and other therapeutic uses.

Broadly stated the present invention relates to an antibody composition comprising antibodies specific for glycophorin A, CD3, CD24, CD16, CD14, and optionally CD45RA, CD36, CD56, CD2, CD19, CD66a and/or CD66b.

The present invention also broadly contemplates a process for enriching and recovering human hematopoietic progenitor cells and stem cells in a sample containing human hematopoietic differentiated, progenitor, and stem cells comprising reacting the sample with an antibody composition containing antibodies capable of binding to the antigens glycophorin A, CD3, CD24, CD16, and CD14, and optionally CD45RA, CD36, CD56, CD2, CD19, CD66a and/or CD66b under conditions so that cell conjugates are formed between the antibodies and cells in the sample having the antigens glycophorin A, CD3, CD24, CD16, and CD14, and optionally CD45RA, CD36, CD56, CD2, CD19, CD66a and/or CD66b on their surfaces; removing the cell conjugates; and recovering a cell preparation which is enriched in human hematopoietic progenitor cells and stem cells.

The present invention also relates to a kit useful in performing the process of the invention comprising antibodies specific for glycophorin A, CD3, CD24, CD16, CD14, and optionally CD45RA, CD36, CD56, CD2, CD19, CD66a and/or CD66b, and instructions for performing the process of the invention. The invention further relates to cell preparations obtained in accordance with the process of the invention. The invention still further contemplates a method of using the antibody composition of the invention in a negative selection method to recover a cell preparation which is enriched in human hematopoietic progenitor and stem cells.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will now be described with reference to the accompanying drawings, in which.

DETAILED DESCRIPTION OF THE INVENTION

I. Hematopoietic Cell Types

Figure 1:
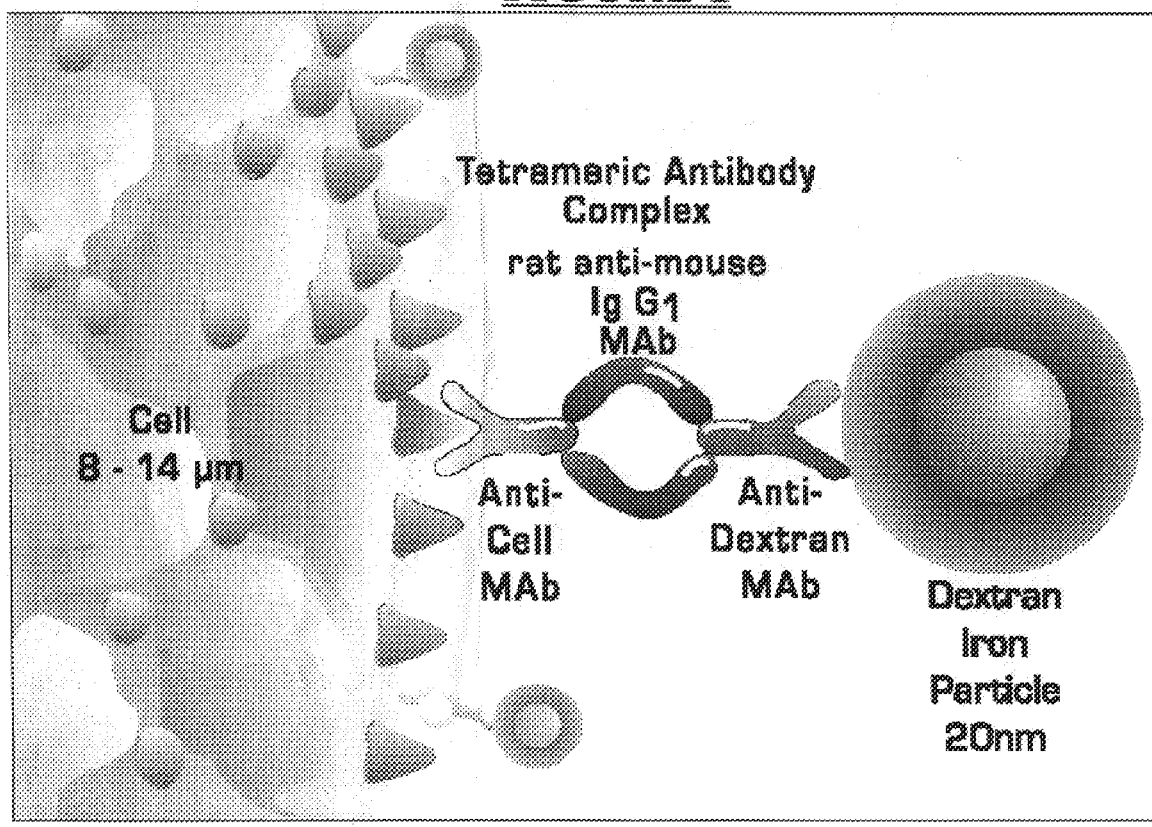
FIG. 1 is a schematic representation of magnetic cell labeling using tetrameric antibody complexes and colloidal dextran iron.

The term "differentiated cells" used herein refers to human hematopoietic cells which have limited or no proliferative capacity. Differentiated cells represent specialized end cells that are found in blood, and their immediate precursors.

The term "progenitor cells" used herein refers to cells which are the immediate precursors of the differentiating cells. Most of the progenitor cells differentiate along a single lineage but they may have quite extensive proliferative capacity. Progenitor cells appear morphologically as blast cells, and they typically do not have specific features of the hematopoietic lineage to which they are committed.

The term "stem cells" used herein refers to the cells from which progenitor cells are derived. Stem cells are defined by their ability to self-renew as well as to generate daughter cells of any of the hematopoietic lineages. Stem cells with long term hematopoietic reconstituting ability can be distinguished by a number of physical and biological properties from differentiated cells and progenitor cells (Hodgson, G. S. & Bradley, T. R., Nature, Vol. 281, pp. 381–382; Visser et al., J. Exp. Med., Vol. 59, pp. 1576–1590, 1984; Spangrude et al., Science, Vol. 241, pp. 58–62, 1988; Szilvassy et al., Blood, Vol. 74, pp. 930–939, 1989; Ploemacher, R. E. & Brons, R. H. C., Exp. Hematol., Vol. 17, pp. 263–266, 1989).

The presence of stem cells and progenitor cells in a cell preparation may be detected by their ability to produce colony-forming cells in culture. They may also be detected by screening for the CD34 antigen which is a positive marker for early hematopoietic cells including colony forming cells and stem cells. Primitive hematopoietic stem cells with long term hematopoietic reconstituting ability can be identified by determining the number of clonogenic cells present after 5 to 8 weeks in long term cultures (Sutherland et al., Blood, Vol. 74, p. 1563, 1986; Udomsakdi et al., Exp. Hematol., Vol. 19, p. 338, 1991; and, Sutherland et al., Proc. Natl. Acad. Sci., Vol. 87, p. 3584, 1990).

II. Antibody Composition

As hereinbefore mentioned, the invention relates to an antibody composition comprising antibodies specific for the antigens glycophorin A, CD3, CD24, CD16, CD14, and optionally CD45RA, CD36, CD56, CD2, CD19, CD66a and/or CD66b which are present on the surface of human differentiated cells.

In an embodiment of the invention, an antibody composition is provided for enriching and recovering human hematopoietic progenitor and stem cells from fresh bone marrow consisting essentially of antibodies specific for glycophorin A, CD3, CD24, CD16, CD14, CD66a and CD66b. In a second embodiment, an antibody composition is provided for enriching and recovering human hematopoietic progenitor and stem cells from previously frozen bone marrow consisting essentially of antibodies specific for glycophorin A, CD3, CD24, CD16, and CD14. In a further embodiment of the invention, an antibody composition is provided for enriching and recovering human hematopoietic progenitor and stem cells from peripheral or cord blood consisting essentially of antibodies specific for glycophorin A, CD3, CD24, CD16, CD14, CD66a, CD66b, CD56 and CD2.

Pluripotent stem cells and committed progenitors express CD34, and this CD34 compartment can be subdivided using antibodies to a variety of cell surface markers. Stem cells co-purify in a population of CD34$^+$ cells which lack or have low expression of certain lineage markers (CD38, CD33, CD45RA, CD71, CD36 and HLA-DR) (Craig et al. 1994, British Journal of Haematology, 88:24–30; Lansdorp, P. AI. and Dragowska, W. (1992) J. Exp. Med. 175:1501–1509; Sutherland, H, J., et al. (1989) Blood 74.1563–1570). Antibodies recognizing these antigens can be included in the antibody composition to further enrich for stem cells, while losing some of the committed mature CD34$^+$ cells. Preferably, anti-CD45RA and anti-CD36 are included in the antibody composition.

Within the context of the present invention, antibodies are understood to include monoclonal antibodies and polyclonal antibodies, antibody fragments (e.g., Fab, and F(ab')$_2$) and recombinantly produced binding partners. Antibodies are understood to be reactive against a selected antigen on the surface of a differentiated cell if they bind with an affinity (association constant) of greater than or equal to $10^7 M^{-1}$.

Polyclonal antibodies against selected antigens on the surface of differentiated cells may be readily generated by one of ordinary skill in the art from a variety of warm-blooded animals such as horses, cows, various fowl, rabbits, mice, or rats.

Preferably, monoclonal antibodies are used in the antibody compositions of the invention. Monoclonal antibodies specific for selected antigens on the surface of differentiated cells may be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques).

Similarly, binding partners may be constructed utilizing recombinant DNA techniques. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. The primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the $V_H$ and $V_L$ domains may be produced (See Bird et al., Science 242:423–426, 1988). In addition, such techniques may be utilized to change a "murine" antibody to a "human" antibody, without altering the binding specificity of the antibody.

Antibodies against selected antigens on the surface of differentiated cells may also be obtained from commercial sources.

Antibodies may be selected for use in the antibody compositions of the invention based on their ability to deplete targeted differentiated cells and recover non-targeted cells (i.e. progenitor and stem cells, or specific differentiated cells) in magnetic cell separations as more particularly described herein, and in co-pending U.S. Pat. No. 5,514,390, which is incorporated in its entirety herein by reference. In general, an antibody is selected that gives approximately a 3 log depletion of differentiated cells, with greater than 75% recovery of CD34$^+$ cells (bone marrow, mobilized blood and cord blood) or non-targeted lymphocytes (steady state blood), in test magnetic cell separations as described herein.

The anti-glycophorin A antibodies contained in the antibody composition of the invention are used to label erythrocytes. Examples of monoclonal antibodies specific for glycophorin A are 10F7MN (U.S. Pat. No. 4,752,582, Cell lines: ATCC accession numbers HB-8473, HB-8474, and HB-8476), and D2.10 (Immunotech, Marseille, France). The concentration of antiglycophorin A antibodies used in the antibody composition are generally less than the concentration that will cause agglutination (i.e. 3–10 $\mu$g/ml). Preferably the concentration of antiglycophorin A antibodies used in the antibody composition is between about 0.5 to 5 $\mu$g/ml, preferably 1 to 2 $\mu$g/ml.

Monoclonal antibodies against CD24, CD3, CD19, CD20, CD56, CD2 in the antibody composition of the invention are used to label B and T lymphocytes and NK cells. Examples of monoclonal antibodies specific for CD24, CD3, CD19, CD20, CD56, and CD2, are 32D12 (Dr. Steinar Funderud, Institute for Cancer Research, Dept. of Immunology, Oslo, Norway,) and ALB9 (Immunotech, Marseille, France); UCHT1 (Immunotech, Marseille, France) and Leu-4 (Becton Dickinson, Mountain View, Calif.); J4.119 (Immunotech, Marseille, France) and Leu-12 (Becton Dickinson, Mountain View, Calif.); MEM97 (Dr. Horejsi, Institute of Molecular Genetics Academy of Sciences of the Czech Republic, Praha, Czech Republic, or Cedarlane Laboratories, Hornby, Ontario, Canada) and Leu-16 (Becton Dickinson, Mountain View, Calif.); T199 (Immunotech, Marseille, France); and 6F10.3 (Immunotech, Marseille, France), respectively. The concentration of each of the monoclonal antibodies against CD24, CD3, CD19, CD20, CD56, CD2 contained in the antibody composition is between about 0.5 to 5 $\mu$g/ml, preferably 2 to 3 $\mu$g/ml.

Monoclonal antibodies against CD14, CD16, CD66a and CD66b in the antibody compositions of the invention are used to label monocytes. Examples of monoclonal antibodies specific for CD14, CD16, CD66a and CD66b, are MEM15 and MEM18 (Dr. Vaclav Horejsi, Institute of Molecular Genetics Academy of Sciences of the Czech Republic, Praha, Czech Republic; Cedarlane Laboratories, Hornby, Ontario, Canada); MEM154 (Dr. Vaclav Horejsi, Institute of Molecular Genetics Academy of Sciences of the Czech Republic, Praha, Czech Republic; Cedarlane Laboratories, Hornby, Ontario, Canada), Leu-11a (Becton Dickinson, Mountain View, Calif.), and 3G8 (Immunotech, Marseille, France); CLB/gran10 (CLB, Central Laboratory of the Netherlands, Red Cross Blood Transfusion Service); and, B13.9 (CLB, Central Laboratory of the Netherlands, Red Cross Blood Transfusion Service) and 80H3 (Immunotech, Marseille, France), respectively. The concentration of each of the monoclonal antibodies against CD14, CD16, CD66a and CD66b contained in the antibody composition is between about 0.5 to 5 $\mu$g/ml, preferably 2–3 $\mu$g/ml.

Monoclonal antibodies against CD45RA and CD36 are used to label T-cells, B-cells, granulocytes, platelets, monocytes, differentiated erythroid precursors, and some committed mature progenitors, to further enrich for stem cells. Examples of monoclonal antibodies against CD45RA and CD36 are 8D2.2 (StemCell Technologies, Vancouver, Canada, Craig et al., 1994, British Journal of Haematology, 88:24–30.), Leu-18 (Becton Dickinson, Mountain View, Calif.); and, FA60152 (Immunotech, Marseille, France) and IVC7 (CLB, Central Laboratory of the Netherlands Red Cross Blood Transfusion Service), respectively. The concentration of each of the monoclonal antibodies against CD45R and CD36 contained in the antibody composition is between about 0.5 to 5 $\mu$g/ml, preferably 1 to 3 $\mu$g/ml.

Table 2 sets out the most preferred monoclonal antibodies, their sources and concentrations, for use in the antibody compositions of the invention.

In most preferred embodiments of the invention the antibody composition comprises the monoclonal antibodies designated D2.10, UCHT1, MEM15, 3G8, ALB9, 80H3, J4.119, 6F10.3, T199, 8D2.2 and FA60152 or comprises the monoclonal antibodies designated 10F7MN, UCHT1, 32D12, MEM154, MEM15, 80H3 or B13.9, T199, 6F10.3, J4.119, and optionally, 8D2.2 and 1VC7.

Antibody compositions in accordance with the present invention may be prepared which lack antibodies to a specific differentiated cell type or lineage committed cell. For example, an antibody composition may be prepared which does not contain antibodies to the CD14, CD16, CD66a and CD66b antigens which are specific to monocytes. This composition may be used to prepare a cell preparation which is enriched for monocytes. Other examples of antibody compositions which can be used to prepare cell populations enriched for monocytes, B-cells, T-cells, CD4$^+$ T-cells, CD8$^+$ T-cells, and NK cells are set out in Table 3.

III. Process for Preparing Cell Preparations Enriched in Progenitor/Stem Cells or a Differentiated Cell Type The antibody composition of the invention may be used to enrich and recover cell preparations enriched in human hematopoietic stem cells and progenitor cells. In accordance with the process of the invention, a sample is reacted with an antibody composition of the invention; under suitable conditions, cell conjugates form between the antibodies contained in the antibody composition which are specific for selected antigens on the surface of differentiated cells, and the cells in the sample containing the antigens on their surface; and the cell conjugates are removed to provide a cell preparation enriched in human progenitor/stem cells.

Conditions which permit the formation of cell conjugates may be selected having regard to factors such as the nature and amounts of the antibodies in the antibody composition, and the estimated concentration of targeted differentiated cells in the sample.

The antibodies in the antibody composition may be labelled with a marker or they may be conjugated to a matrix. Examples of markers are biotin, which can be removed by avidin bound to a support, and fluorochromes, e.g. fluorescein, which provide for separation using fluorescence activated sorters. Examples of matrices are magnetic beads, which allow for direct magnetic separation (Kernshead 1992), panning surfaces e.g. plates, (Lebkowski, J. S., et al., (1994), J. of Cellular Biochemistry supple. 18b:58), dense particles for density centrifugation (Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.), adsorption columns (Berenson et al. 1986, Journal of Immunological Methods 91:11–19.), and adsorption membranes (Norton et al. 1994). The antibodies may also be joined to a cytotoxic agent such as complement or a cytotoxin, to lyse or kill the targeted differentiated cells.

The antibodies in the antibody composition may be directly or indirectly coupled to a matrix. For example, the antibodies in the composition of the invention may be chemically bound to the surface of magnetic particles for example, using cyanogen bromide. When the magnetic particles are reacted with a sample, conjugates will form between the magnetic particles with bound antibodies specific for antigens on the surfaces of the differentiated cells, and the differentiated cells having the antigens on their surfaces.

Alternatively, the antibodies may be indirectly conjugated to a matrix using antibodies. For example, a matrix may be coated with a second antibody having specificity for the antibodies in the antibody composition. By way of example, if the antibodies in the antibody composition are mouse IgG antibodies, the second antibody may be rabbit anti-mouse IgG.

The antibodies in the antibody composition may also be incorporated in antibody reagents which indirectly conjugate to a matrix. Examples of antibody reagents are bispecific antibodies, tetrameric antibody complexes, and biotinylated antibodies.

Bispecific antibodies contain a variable region of an antibody in the antibody composition of the invention, and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (1986, PNAS (USA) 83:1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

A tetrameric immunological complex may be prepared by mixing a first monoclonal antibody which Is capable of binding to at least one antigen on the surface of a matrix, and a second monoclonal antibody from the antibody composition of the invention. The first and second monoclonal antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

The antibodies of the invention may be biotinylated and indirectly conjugated to a matrix which is labelled with (strept) avidin. For example, biotinylated antibodies contained in the antibody composition of the invention may be used in combination with magnetic iron-dextran particles that are covalently labelled with (strept) avidin (Miltenyi S. et al., Cytometry 11:231, 1990). Many alternative indirect ways to specifically cross-link the antibodies in the antibody composition and matrices would also be apparent to those skilled in the art.

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-inked with divinylbenzene. The core portion is generally too small to hold a permanent magnetic field. The ferrofluids become magnetized when placed in a magnetic field. Examples of ferrofluids and methods for preparing them are described by Kemshead J. T. (1992) in J. Hematotherapy, 1:35–44, at pages 36 to 39, and Ziolo et al. Science (1994) 257:219 which are incorporated herein by reference. Colloidal particles of dextran-iron complex are preferably used in the process of the invention.(See Molday, R. S. and McKenzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother. 2:297 (1993); and U.S. Pat. No. 4,452,733, which are each incorporated herein by reference).

FIG. 1 is a schematic representation of magnetic cell labeling using tetrameric antibody complexes and colloidal dextran iron.

In accordance with the magnetic separation method, the sample containing the progenitor and stem cells to be recovered, is reacted with the above described antibody reagents, preferably tetrameric antibody complexes, so that the antibody reagents bind to the targeted differentiated cells present in the sample to form cell conjugates of the targeted differentiated cells and the antibody reagents. The reaction conditions are selected to provide the desired level of binding of the targeted differentiated cells and the antibody reagents. Preferably the sample is incubated with the antibody reagents for a period of 5 to 60 minutes at either 4° or ambient room temperature. The concentration of the antibody reagents is selected depending on the estimated concentration of the targeted differentiated cells in the sample. Generally, the concentration is between about 0.1 to 50 μg/ml of sample. The magnetic particles are then added and the mixture is incubated for a period of about 5 minutes to 30 minutes at the selected temperature. The sample is then ready to be separated over a magnetic filter device. Preferably, the magnetic separation procedure is carried out using the magnetic filter and methods described in co-pending U.S. Pat. No. 5,514,340 to Lansdorp and Thomas which is incorporated in its entirety herein by reference.

The sample containing the magnetically labelled cell conjugates is passed through the magnetic filter in the presence of a magnetic field. In a preferred embodiment of the invention, the magnet is a solenoid electromagnet with a 3" diameter bore and having a magnetic field of 0.5–2 Tesla. The magnetically labelled cell conjugates are retained in the high gradient magnetic column and the materials which are not magnetically labelled flow through the column after washing with a buffer.

The preparation containing non-magnetically labelled cells may be analyzed using procedures such as flow cytometry. The ability of the cells in the preparation to produce colony-forming cells or long term culture initiating cells (LTCIC) in culture may also be assessed. The efficiency of the separation procedure may also be determined by monitoring the recovery of CD34$^+$ cells, CD34$^+$CD38$^-$ cells and colony forming cells.

The antibody compositions of the invention may also be used to prepare a cell preparation which is enriched for a specific differentiated cell type. This is achieved by using antibody compositions which lack antibodies to the specific differentiated cell type, in the above described processes of the invention. Particular embodiments of these processes of the invention are set out below. It will be appreciated that the markers, matrices, antibody reagents, and procedures described herein may be used in these processes to facilitate recovery of cell preparations enriched for a specific differentiated cell type. Examples of antibodies which may be used in these processes are set out in Table 2.

In accordance with one embodiment of the invention, a process is provided for enriching and recovering monocytes from a blood or bone marrow sample comprising reacting the sample with an antibody composition containing antibodies capable of binding to the antigens glycophorin A, CD2, CD3, CD56, and CD24 or CD19, and optionally CD66b under conditions so that cell conjugates are formed between the antibodies and the cells in the sample having the antigens glycophorin A, CD2, CD3, CD56, and CD24 or CD19 and optionally CD66b, on their surfaces; removing the cell conjugates; and recovering a cell preparation which is enriched in monocytes.

In accordance with another embodiment of the invention, a process is provided for enriching and recovering B-cells from a blood or bone marrow sample comprising reacting the sample with an antibody composition containing antibodies capable of binding to the antigens glycophorin A, CD2, CD3, CD56, and CD14, and optionally CD66b under conditions so that cell conjugates are formed between the antibodies and the cells in the sample having the antigens glycophorin A, CD2, CD3, CD56, and CD14 and optionally CD66b, on their surfaces; removing the cell conjugates, and recovering a cell preparation which is enriched in B-cells.

In accordance with another embodiment of the invention, a process is provided for enriching and recovering T-cells from a blood or bone marrow sample comprising reacting the sample with an antibody composition containing antibodies capable of binding to the antigens glycophorin A, CD24 or CD19, CD56, and optionally CD66b under conditions so that cell conjugates are formed between the antibodies and the cells in the sample having the antigens glycophorin A, CD24 or CD19, CD56, and optionally CD66b, on their surfaces; removing the cell conjugates; and recovering a cell preparation which is enriched in T-cells.

In accordance with yet another embodiment of the invention, a process is provided for enriching and recovering CD4$^+$T-cells from a blood or bone marrow sample comprising reacting the sample with an antibody composition containing antibodies capable of binding to the antigens glycophorin A, CD24 or CD19, CD56, CD8, and optionally CD66b under conditions so that cell conjugates are formed between the antibodies and the cells in the sample having the antigens glycophorin A, CD24 or CD19, CD56, CD8, and optionally CD66b, on their surfaces; removing the cell conjugates; and recovering a cell preparation which is enriched in CD4$^+$T-cells.

In accordance with a further embodiment of the invention, a process is provided for enriching and recovering CD8$^+$T-cells from a blood or bone marrow sample comprising reacting the sample with an antibody composition containing antibodies capable of binding to the antigens glycophorin A, CD24 or CD19, CD56, CD4, and optionally CD66b under conditions so that cell conjugates are formed between the antibodies and the cells in the sample having the antigens glycophorin A, CD24 or CD19, CD56, CD4, and optionally CD66b, on their surfaces; removing the cell conjugates; and recovering a cell preparation which is enriched in CD8$^+$T-cells.

In accordance with a still further embodiment of the invention, a process is provided for enriching and recovering NK-cells from a blood or bone marrow sample comprising reacting the sample with an antibody composition containing antibodies capable of binding to the antigens glycophorin A, CD24 or CD19, and CD3, and optionally CD66b under conditions so that cell conjugates are formed between the antibodies and the cells in the sample having the antigens glycophorin A, CD24 or CD19, and CD3, and optionally CD66b, on their surfaces; removing the cell conjugates; and recovering a cell preparation which is enriched in NK-cells.

IV. Uses of the Compositions and Processes of the Invention

The device and processes of the invention may be used in the processing of biological samples including blood in particular, cord blood and whole blood. It has also been found that the antibody compositions of the invention can be used to prepare hematopoietic progenitor and stem cell preparations from bone marrow samples, including previously frozen bone marrow samples.

The processes of the invention are preferably used to deplete or purge erythrocytes, B and T lymphocytes, monocytes, NK cells, and granulocytes, from samples to prepare hematopoietic progenitor and stem cell preparations for use in transplantation as well as other therapeutic methods that are readily apparent to those of skill in the art. For example, bone marrow or blood can be harvested from a donor in the case of an allogenic transplant and enriched for progenitor and stem cells by the processes described herein.

Using the process of the invention it is possible to recover a highly purified preparation of human hematopoietic stem/progenitor cells. In particular, a hematopoietic cell population containing greater than 50% of the hematopoietic progenitor/stem cells present in the original sample, and which is depleted of differentiated cells in the original sample by approximately 3 logarithms may be obtained. The human hematopoietic progenitor and stem cells in the preparation are not coated with antibodies, or modified making them highly suitable for transplantation and other therapeutic uses that are readily apparent to those skilled in the art.

The cell preparations obtained using the processes of the invention may be used to isolate and evaluate factors associated with the differentiation and maturation of human hematopoietic cells. The cell preparations may also be used to determine the effect of a substance on cell growth and/or differentiation into a particular lineage.

The antibody compositions and processes of the invention may also be used to prepare a cell preparation from samples such as blood and bone marrow, which is enriched in a selected differentiated cell type. This will enable studies of specific cell to cell interactions including growth factor production and responses to growth factors. It will also allow molecular and biochemical analysis of specific cells types. Cell preparations enriched in NK cells and T-cells may also be used in immune therapy against certain malignancies.

The following non-limiting examples are illustrative of the present invention:

EXAMPLES

Example 1

Method for Evaluating Antibody Combinations

Suspensions of normal human bone marrow, human cord blood, mobilized human peripheral blood and previously frozen human bone marrow were labeled with tetrameric antibodies and colloidal dextran iron for magnetic cell depletions. Monoclonal antibodies recognizing lineage specific cell surface antigens were mixed with a mouse $IgG_1$ anti-dextran antibody (Thomas, T. E., et al. (1992), J. Immunol Methods 154:245;252) and a rat $IgG_1$ monoclonal antibody which recognizes the Fc portion of the mouse $IgG_1$ molecule (TFL-P9) (Lansdorp, P. M., and Thomas, T. E. (1990), Mol. Immunol. 27:659–666). Tetrameric antibody complexes (Lansdorp, P. M., and Thomas, T. E. (1990), Mol. Immunol. 27;659–666; U.S. Pat. No. 4,868,109 to Lansdorp) spontaneously form when mouse $IgG_1$ molecules (the lineage specific monoclonal antibody and anti-dextran) are mixed with P9. A proportion of these tetrameric antibody complexes are bifunctional, recognizing an antigen on the surface of the target cell on one side and dextran (part of the magnetic colloidal dextran iron) on the other. Tetrameric antibody complexes were made for all the antibodies in the lineage cocktail. FIG. 1 shows a schematic representation of magnetic cell labeling using tetrameric antibody complexes and colloidal dextran iron.

Cells were labeled for separation (1–5×10$^7$ cells/ml) by incubating them with the desired combination of tetramers for 30 min on ice followed by a 30 min incubation with colloidal dextran iron (final OD450=0.6) (Molday and MacKenzie 1982). The cells were then passed through a magnetic filter (U.S. Pat. No. 5,514,340; inventors Lansdorp and Thomas) at 1 cm/min. The magnetically labeled cells bind to the filter and the unlabeled cells pass through. FIG. 1 shows a schematic representation of magnetic cell labeling using tetrameric antibody complexes and colloidal dextran iron.

Figure 2:
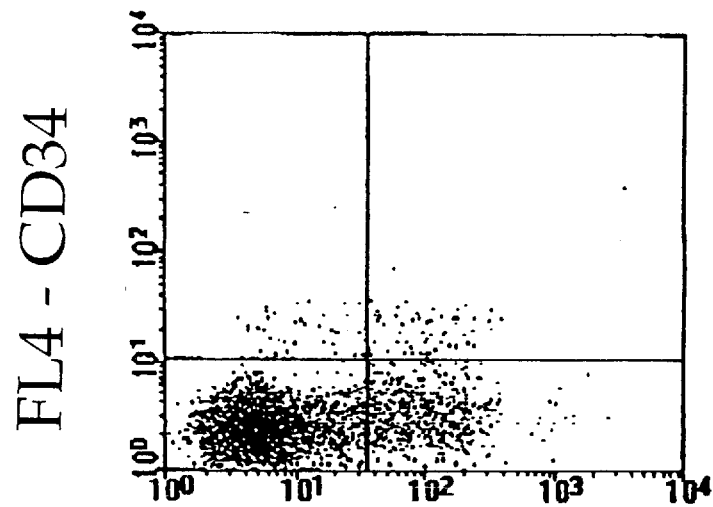
FIG. 2A shows a Fluorescence Activated Cell Sorting (FACS) profile of normal bone marrow before progenitor enrichment using lineage depletion where the vertical axis shows staining with CY5-antiCD34 and the horizontal axis phycoerythrin-antiCD38.
FIG. 2B shows a Fluorescence Activated Cell Sorting (FACS) profile of normal bone marrow after progenitor enrichment using lineage depletion where the vertical axis shows staining with CY5-antiCD34 and the horizontal axis phycoerythrin-antiCD38.
Figure 2:
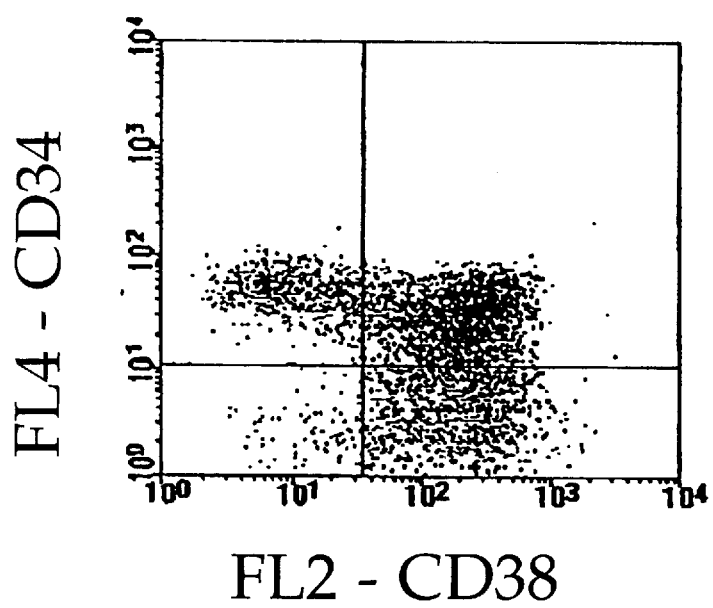

The flow through fraction is collected and analyzed for hematopoietic colony forming cells (CFU-GM, CFU-C, LTCIC) (Eaves, C. J. and Eaves, A. J. (1992) In: Current Therapy in Hematology-Oncology, Fourth Edition pp. 159–167), CD34+ cells, and CD34+CD38– cells. The enrichment of these cell types depends on how well the antibody cocktail has targeted other cells for removal. Each antibody cocktail was evaluated for the purity and recovery of colony forming cells, CD34+ cells, and CD34+CD38– cells. FIG. 2 shows a FACS profile of normal bone marrow before and after progenitor enrichment via lineage depletion.

Example 2

Antibodies for the Enrichment of Progenitor Cells (Progenitor Cocktail)

The results of numerous cell separations identified a combination of lineage specific antibodies that produce the maximum enrichment and recovery of CD34+ cells and colony forming cells.

Targeting Erythrocytes—Anti-glycophorin A antibodies were used to label erythrocytes for depletion. Many of these antibodies will cause agglutination at moderate to high antibody concentrations (3–10 µg/ml). It was found that cells could be effectively targeted for magnetic depletion with concentrations of anti-glycophorin antibody that were several fold lower than that which caused agglutination.

Targeting Lymphocytes—B, T, and NK cells were targeted with monoclonal antibodies against CD24, CD3, CD19, CD20, CD56, CD2. Initial depletions of mobilized peripheral blood using just anti-CD24 and CD3 for lymphocyte depletion showed that a proportion of the CD34 negative cells in the purified fraction were CD56 positive (NK cells). Subsequent tests with and without anti-CD56 increased the purity of CD34+ cells in the recovered fraction by 12–20%. Adding an anti-CD2 to the cocktail increased the purity an additional 12–13%. Anti-CD2 and anti-CD56 had no significant effect on lineage depletions of fresh bone marrow. It is likely that bone marrow does not have as many CD3–CD2+ and CD3–CD56+ cells. Anti-CD2 and anti-CD56 are added to the depletion cocktails for mobilized peripheral blood but not bone marrow.

Antibodies against CD24 were sufficient to target all detectable B-cells for depletion. Adding anti-CD19 gave no additional enrichment of CD34+ cells from mobilized peripheral blood or bone marrow. Substituting CD19 for CD24 in separations of fresh bone marrow had no effect on the enrichment or recovery of C34+ cells, hematopoietic colony forming cells and LTCIC, Replacing anti-CD24 with anti-CD20 or both anti-CD19 and anti-CD20 had no significant effect on separations of mobilized peripheral blood. An effect was seen in a separation with cord blood; when anti-CD24 was replaced with anti-CD19, the purity was decreased 21%, but recovery of CD34+ cells was increased 28%.

Targeting Mature Myeloid Cells—Monocytes were effectively targeted with an antibody against CD14 in all cell suspensions tested. The removal of granulocytes from peripheral blood and fresh bone marrow was more efficient using both anti-CD16 and anti-CD66b rather than anti-CD16 alone and adding anti-CD66a gave an additional 10% enrichment of CD34+ cells from fresh bone marrow and 20% enrichment for peripheral blood. Anti-CD16 alone was sufficient to deplete the granulocytes from previously frozen marrow. Adding anti-CD41 or CD42a did not increase the purity of CD34+ cells in either peripheral blood or bone marrow.

Example 3

Antibodies for the Enrichment of Stem Cells (Stem Cell Cocktail)

Both pluripotent stem cells and committed progenitors express CD34, but the CD34 compartment can be further subdivided using a variety of cell surface markers to isolate these cell types. Stem cells co-purify in a population of CD34+ cells which lack or have low expression of certain lineage markers (CD38, CD33, CD45RA, CD71, CD36 and HLA-DR) (Craig et al. 1994, British Journal of Haematology, 88:24–30; Lansdorp, F. AI. and Dragowska, W. (1992), J. Exp. Med. 175:1501–1509; Sutherland, H. J., et al. (1989), Blood 74.1563–1570.). If antibodies recognizing these antigens are included in the lineage cocktail one can further enrich for stem cells while losing some of the committed mature CD34+ cells. Antibodies to CD36 and CD45RA were added to the lineage cocktail to specifically enrich for stem cells. The recovery of CD34+ CD38– cells and LTCICs were monitored to determine the efficiency of the lineage depletions with the "stem cell cocktail".

Including anti-CD45RA in the stem cell cocktail does not negate the need for anti-CD24 in the cocktail nor does anti-CD36 allow the removal of CD66a. Adding anti-CD36 did increase the purity of CD34+CD38−cells in separations of previously frozen bone marrow by 15%. The addition of anti-transferrin (CD71) antibody to the cocktail resulted in very poor recovery of CD34+ CD38− cells, and LTCIC as well as producing a significant number of dead cells in the enriched fraction (viability normally >95%). Separations of previously frozen bone marrow with the stem cell cocktail produced a cell suspension which is approximately 30% CD34+ CD38− with 30% recovery of these cells, Similar separations with mobilized peripheral blood gave 15% purity and 72% recovery.

Example 4

Different Antibodies to the Same Antigen

The enrichment of hematopoietic progenitor cells via lineage depletion is not only dependent on the number of types of committed cells that are targeted but also the effectiveness of this targeting and subsequent removal using magnetic separation or other antibody mediated techniques. It was found that different antibodies recognizing the same antigen may reproducibly produce different degrees of progenitor enrichment, The anti-CD24 antibody 32D12 produced better results in lineage depletions than ALB9 (also anti-CD24); the purity of the enriched cell suspension increased 10% in a separation with cord blood. In cell depletions with a single tetramer type, 32D12 out performed ALB9 and anti-glycophorin antibody 10P7MN out performed anti-glycophorin antibody D2.10 although switching anti-glycophorin antibodies in a lineage depletion had no significant effect.

The criteria for choosing a particular antibody at a given concentration is its performance in a magnetic cell separation which equates to the maximum depletion of antibody targeted cells with the maximum recovery of non-target cells. Often depletion of antibody targeted cells increases with antibody concentration but so does the non-specific labeling of cells. In general, the result looked for was a 3 log depletion with greater than 75% recovery of CD34+ cells or non-targeted lymphocytes if the test cell suspension was steady state peripheral blood. The performance in a cell separation typically mimicked the degree of specific cell labeling and the degree on non-specific labeling measured by FACS (sheep anti-mouse FITC staining). Staining experiments were often run to eliminate antibodies (specific staining low, non-specific staining high) and reduce the number of antibody concentrations to be tested in cell separations.

While what is shown and described herein constitutes various preferred embodiments of the subject invention, it will be understood that various changes can be made to such embodiments without departing from the subject invention, the scope of which is defined in the appended claims.

TABLE 1

Optimal Antibody Cocktail for the Enrichment of Hematopoietic Progenitors

| Cell Suspension | optimum antibody cocktail anti- | % purity CD34+ cells | % recovery CD34+ cells |
|---|---|---|---|
| fresh bone marrow | gly*, CD3, CD24, CD16, CD14, CD66a, CD66b, | 39,44,38 | 67,48,55 |
| previously frozen bone | gly, CD3, CD24, CD16, CD14, | 64,46,50,53 | 85,55,82,64 |
| marrow mobilized peripheral blood | gly, CD3, CD24, CD16, CD14, CD66a, CD66b, CD56, CD2, | 51,50,57 | 43,49,85 |
| cord blood | gly, CD3, CD24, CD16, CD14, CD66a, CD66b, CD56, CD2, | 56,88,58,55,63 | 75,85,53,67,48 |

*gly = glycophorin A

TABLE 2

Antibodies used in Lineage Depletions

| Antigen | Antibody | Source | Concentration ug/ml |
|---|---|---|---|
| glycophorin | 10F7MN* | U.S. Pat. No. 4,752,582 | 1 |
| | D2.10 | IMMUNOTECH, Marseille, France | 2 |
| CD2 | 6F10.3 | IMMUNOTECH, Marseille, France | 3 |
| CD3 | UCHT1 | IMMUNOTECH, Marseille, France | 3 |
| | Leu-4 | Becton Dickinson Immunocytometry, Mountain View, Calif. | |
| CD4 | Leu-3a | Becton Dickinson Immunocytometry, Mountain View, Calif. | |
| CD8 | Leu-2a | Becton Dickinson Immunocytometry, Mountain View, Calif. | |
| | OKT3 | BioDesigns | |
| CD14 | MEM 15 | Dr. Vaclav Horejsi, Institute of Molecular Genetics Academy of Sciences of the Czech Republic, Praha, Czech Republic; Cedarlane Laboratories Hornby, Ontario, Canada | 2 |
| | MEM 18 | | 2 |
| CD16 | MEM 154* | Dr. Vaclav Horejsi, Institute of Molecular Genetics Academy of Sciences of the Czech Republic, Praha, Czech Republic; Cedarlane Laboratories Hornby, Ontario, Canada | 2 3 |
| | 3G8 | IMMUNOTECH, Marseille, France | |
| | Leu-11a | Becton Dickinson Immunocytometry, Mountain View, Calif. | |
| CD19 | J4.119 | IMMUNOTECH, Marseille, France | 3 |
| | Leu-12 | Becton Dickinson Immunocytometry, Mountain View, Calif. | |
| CD20 | MEM97 | Dr. Vaclav Horejsi, Institute of Molecular Genetics Academy of Sciences of the Czech Republic, Praha, Czech Republic; Cedarlane Laboratories Hornby, Ontario, Canada | 3 |
| | Leu-16 | Becton Dickinson Immunocytometry, Mountain View, Calif. | |
| CD24 | 32D12* | Dr. Steinar Funderud, Institute for Cancer Research, Dept. of Immunology, Oslo, Norway | 2 3 |

TABLE 2-continued

Antibodies used in Lineage Depletions

| Antigen | Antibody | Source | Concentration ug/ml |
|---|---|---|---|
| | ALB9 | IMMUNOTECH, Marseille, France | |
| CD36 | FA60152 | IMMUNOTECH, Marseille, France | 3 |
| | IVC7 | CLB, Central Laboratory of the Netherlands, Red Cross Blood Transfusion Service | |
| CD41 | PI1.64 | Kaplan, 5th International Workshop on Human Leukocyte Differentiation Antigens | 3 |
| CD42a | Beb1 | Becton Dickinson Immunocytometry, Mountain View, Calif. | 3 |
| CD45RA | 8D2.2 | Craig et al. 1994, StemCell Technologies, Vancouver, Canada | 1 |
| | Leu-18 | Becton Dickinson Immunocytometry, Mountain View, Calif. | |
| CD56 | T199 | IMMUNOTECH, Marseille, France | 3 |
| CD66a | CLB/gran10 | CLB, Central Laboratory of the Netherlands, Red Cross Blood Transfusion Service | 3 |
| CD66b | B13.9 | CLB, Central Laboratory of the Netherlands, Red Cross Blood Transfusion Service | 3 3 |
| | 80H3 | IMMUNOTECH, Marseille, France | |

*preferred antibody based on performance in magnetic cell separations

TABLE 3

Antibody Cocktails to Purify Specific Types of Lineage Committed Cells

| Desired Cell type | source of cells | cocktail of antibodies |
|---|---|---|
| Monocytes | Ficolled Blood | anti-glycophorin, anti-CD2,CD3,CD56, CD24(CD19) |
| | Whole Blood | anti-glycophorin, anti-CD2,CD3,CD56, CD24(CD19),CD66b |
| B-Cells | Ficolled Blood | anti-glycophorin, anti-CD2,CD3,CD56, CD14 |
| | Whole Blood | anti-glycophorin, anti-CD2,CD3,CD56, CD14,CD66b |
| T-Cells | Ficolled Blood | anti-glycophorin, anti-CD24(19),CD56 |
| | Whole Blood | anti-glycophorin, anti-CD24(19),CD56, CD66b |
| CD4+ T-Cells | Ficolled Blood | anti-glycophorin, anti-CD24(19)CD56, CD8 |
| | Whole Blood | anti-glycophorin, anti-CD24(19),CD56, CD8,CD66b |
| CD8+ T-Cells | Ficolled Blood | anti-glycophorin, anti-CD24(19),CD56, CD4 |
| | Whole Blood | anti-glycophorin, anti-CD24(19),CD56, CD4,CD66b |
| NK Cells | Ficolled Blood | anti-glycophorin, anti-CD24(19),CD3 |
| | Whole Blood | anti-glycophorin, anti-CD24(19),CD3, CD66b |

We claim:

1. A negative selection process for enriching and recovering human hematopoietic progenitor cells and human hematopoietic stem cells in a sample containing human hematopoietic differentiated cells, human hematopoietic progenitor cells, and human hematopoietic stem cells comprising:

(a) reacting the sample with an antibody composition containing antibodies capable of binding to the antigens glycophorin A, CD3, CD24, CD16, and CD14 in one step under conditions so that conjugates are formed between the antibodies and cells in the sample containing the antigens glycophorin A, CD3, CD24, CD16, and CD14 on their surfaces;

(b) removing the conjugates; and, (c) recovering a cell preparation which is enriched in human hematopoietic progenitor cells and human hematopoietic stem cells wherein the cell preparation recovered in step (c) has a 3 log depletion of human hematopoietic differentiated cells and is not labeled or coated with antibodies.

2. A process as claimed in claim 1, wherein the antibodies in the antibody composition are monoclonal antibodies.

3. A process as claimed in claim 2 wherein the antibodies in the antibody composition are labelled with a marker or the antibodies are conjugated to a matrix.

4. A process as claimed in claim 3 wherein the antibodies in the antibody composition are labelled with biotin or a fluorochrome.

5. A process as claimed in claim 3 wherein the matrix is magnetic beads, a panning surface, dense particles for density centrifugation, an adsorption column, or an adsorption membrane.

6. A process as claimed in claim 5, wherein each of the monoclonal antibodies in the antibody composition is incorporated in a tetrameric antibody complex which comprises a first monoclonal antibody of a first animal species from the antibody composition containing antibodies capable of binding to the antigens glycophorin A, CD3, CD24, CD16, and CD14, and a second monoclonal antibody of the first animal species which is capable of binding to at least one antigen on the surface of a matrix, which have been conjugated to form a cyclic tetramer with two monoclonal antibodies of a second animal species directed against the Fc-fragments of the antibodies of the first animal species.

7. A process as claimed in claim 6 wherein the antibody composition consists essentially of (a) antibodies specific for glycophorin A, CD3, CD24, CD16, CD14, CD66a and CD66b; or (b) antibodies specific for glycophorin A, CD3, CD24, CD16, CD14, CD66a, CD66b, CD56 and CD2.

8. A process for enriching and recovering human hematopoietic progenitor cells and human hematopoietic stem cells in a sample containing human hematopoietic differentiated cells, human hematopoietic progenitor cells, and human hematopoietic stem cells comprising:

(a) reacting the sample with an antibody composition containing antibodies capable of binding to the antigens glycophorin A, CD3, CD24, CD16, CD14, CD45RA, CD36, CD56, CD2, CD19, CD66a and CD66b in one step under conditions so that conjugates are formed between the antibodies and cells in the sample containing the antigens glycophorin A, CD3, CD24, CD16, CD14, CD19, CD20, CD56, CD2, CD19, CD66a and CD66b on their surfaces;

(b) removing the conjugates; and, (c) recovering a cell preparation which is enriched in human hematopoietic progenitor cells and human hematopoietic stem cells wherein the cell preparation recovered in step (c) has a 3 log depletion of human hematopoietic differentiated cells and is not labeled or coated with antibodies.

9. A process as claimed in claim 8, wherein the antibodies in the antibody composition are monoclonal antibodies.

10. A process as claimed in claim 8 wherein the antibodies in the antibody composition are labelled with a marker or the antibodies are conjugated to a matrix.

11. A process as claimed in claim 8 wherein the antibodies in the antibody composition are labelled with biotin or a fluorochrome.

12. A process as claimed in claim 10 wherein the matrix is magnetic beads, a panning surface, dense particles for density centrifugation, an adsorption column, or an adsorption membrane.

13. A process as claimed in claim 8, wherein each of the monoclonal antibodies in the antibody composition is incorporated in a tetrameric antibody complex which comprises a first monoclonal antibody of a first animal species from the antibody composition containing antibodies capable of binding to the antigens glycophorin A, CD3, CD24, CD16, CD14, CD45RA, CD36, CD56, CD2, CD19, CD66a and CD66b, and a second monoclonal antibody of the first animal species which is capable of binding to at least one antigen on the surface of a matrix, which have been conjugated to form a cyclic tetramer with two monoclonal antibodies of a second animal species directed against the Fc-fragments of the antibodies of the first animal species.

14. A process for enriching and recovering human hematopoietic progenitor cells and human hematopoietic stem cells in a sample containing human hematopoietic differentiated cells, human hematopoietic progenitor cells, and human hematopoietic stem cells as claimed in claim 1 wherein greater than 50% of human hematopoietic progenitor cells and human hematopoietic stem cells are recovered in step (c).

15. A process for enriching and recovering human hematopoietic progenitor cells and human hematopoietic stem cells in a sample containing human hematopoietic differentiated cells, human hematopoietic progenitor cells, and human hematopoietic stem cells as claimed in claim 8 wherein greater than 50% of human hematopoietic progenitor cells and human hematopoietic stem cells are recovered in step (c).

* * * * *

UNITED STATES PATENT AND TRADEMARK OFFICE
CERTIFICATE OF CORRECTION

PATENT NO. : 5,877,299
DATED : March 2, 1999
INVENTOR(S) : Terry Thomas, et al.

It is certified that error appears in the above-identified patent and that said Letters Patent is hereby corrected as shown below:

Column 18, lines 1 and 2, delete "in one step".

Column 18, lines 50 and 51, delete "in one step".

Signed and Sealed this

Sixth Day of July, 1999

Attest:

Q. TODD DICKINSON

*Attesting Officer*  *Acting Commissioner of Patents and Trademarks*